United States Patent [19]

Santasalo

[11] Patent Number: 5,174,970
[45] Date of Patent: Dec. 29, 1992

[54] VESSEL FOR USE IN A STERILIZING METHOD

[75] Inventor: Lauri Santasalo, Helsinki, Finland

[73] Assignee: Sterilinja Oy, Finland

[21] Appl. No.: 475,028

[22] Filed: Feb. 5, 1990

[30] Foreign Application Priority Data

Feb. 6, 1989 [FI] Finland ................ 890551

[51] Int. Cl.⁵ .............................. A61L 2/00
[52] U.S. Cl. .................. 422/292; 422/300; 220/506; 220/87.1
[58] Field of Search ............... 422/292, 300; 220/506, 220/87.1; 99/426, 422; 206/561, 564; 435/297–301

[56] References Cited
U.S. PATENT DOCUMENTS

| | | | |
|---|---|---|---|
| 166,120 | 7/1875 | Malin | 99/422 |
| 1,319,878 | 10/1919 | Lewis | 99/422 |
| 1,921,084 | 8/1933 | Kipe | 422/300 |
| 3,097,070 | 7/1963 | Aldnich et al. | 435/297 |
| 3,326,458 | 6/1967 | Meryman et al. | 220/506 |
| 3,375,047 | 3/1968 | Townsend | 220/506 |
| 3,660,243 | 5/1972 | Young | 435/298 |
| 4,207,286 | 6/1980 | Gut Boucher | 422/28 |
| 4,324,859 | 4/1982 | Saxholm | 435/300 |
| 4,668,633 | 5/1987 | Walton | 435/298 |
| 4,896,772 | 1/1990 | Walter et al. | 206/561 |
| 4,978,004 | 12/1990 | Silverstein et al. | 206/561 |

Primary Examiner—Robert J. Warden
Assistant Examiner—Laura E. Collins
Attorney, Agent, or Firm—Steinberg & Raskin

[57] ABSTRACT

A vessel for containing a sterilizing agent for use in a sterilization method wherein instruments to be sterilized and the liquid sterilizing agent contained in the vessel are located in the chamber of sterilizing apparatus which is closed and heated to evaporate the sterilizing agent and sterilize the instruments. The vessel comprises a central shallow first vessel part defining a central sterilizing agent-containing space which is surrounded by an outer second vessel part defining a supplemental space into which the sterilizing agent will flow should it overflow over the short brim wall of the central sterilizing agent-containing space.

7 Claims, 2 Drawing Sheets

VESSEL FOR USE IN A STERILIZING METHOD

BACKGROUND OF THE INVENTION

This invention relates generally to sterilization apparatus and, more particularly, to vessels for holding liquid sterilizing agents in evaporative sterilizing procedures.

Methods for sterilizing instruments are known in which the instruments to be sterilized are placed on a closable chamber along with an open vessel containing liquid sterilizing agent. After closing the chamber, the temperature is raised to evaporate the sterilizing agent and sterilize the instruments.

A sterilizing method is disclosed in Finnish Application No. 874366 assigned to applicant's assignee, in which the instruments to be sterilized are situated within a closed sterilizing chamber which is then heated to a suitable temperature and into which peracetic acid is either previously provided or introduced. The peracetic acid evaporates under the effect of the raised temperature and acts as a sterilizing agent to sterilize the instruments. Apparatus used in the sterilization procedure described in Finnish Application No. 874366 comprises a sterilizing chamber in which a heater and a vessel for the sterilizing agent are provided. Peracetic acid, a strong oxidizing agent, is used as the sterilizing agent to sterilize the instruments. Since peracetic acid does not corrode stainless steel, and since most instruments today are made of stainless steel, the peracetic acid does not have a corroding effect during the sterilization of such stainless steel instruments.

More particularly, in accordance with the method disclosed in Finnish Application 874366, a fully or partially closed pressure-free chamber is heated to a temperature of about 40° C. by means of a glow lamp, hot-water coil, or small electric resistor. Peracetic acid is placed in a shallow vessel, for example a dish, from which it is evaporated by the effect of the heat conducted through the bottom wall of the chamber. It is also known that sterilization takes placed most reliably in an atmosphere in which the moisture content is higher than in the ambient atmosphere. The objects to be sterilized are placed on shelves within the sterilization chamber, preferably at the end of a working day, whereupon the sterilization technique occurs overnight so that the instruments may be removed from the chamber the next morning.

When the sterilization procedure has been completed, the chamber is emptied in any suitable manner such, for example, as by means of a water aspirator, ventilation hose, or equivalent. The peracetic acid does not cause damage to the environment but decomposes into water, oxygen and vinegar. The vinegar smell, which is a characteristic of peracetic acid, rapidly disappears when the objects sterilized are metallic instruments. Evaporation is slower, however, in the case of softer instruments and therefore they may require ventilation for some time after sterilization.

This sterilization method, however, has the drawback that when the peracetic acid is placed into the sterilization chamber in the shallow dish from which it is to evaporate by heating, it tends to splash over the brim of the vessel. Since almost all modern instruments in use today that are sterilized are made of stainless steel, peracetic acid accidently splashed on such instruments does not cause corrosion. However, thus, the peracetic acid splashes on other objects or onto the floor, it can cause serious corrosion. However, it is difficult to avoid such splashing since the vessel in which it is carried must be a relatively shallow and dish-like in order to maximize evaporation. Therefore, the brim of the vessel defining the space in which the peracetic acid is carried should not be excessively high.

OBJECT OF THE INVENTION

Briefly, it is an object of the present invention to provide new and improved apparatus for use in sterilizing methods and, in particular, new and improved vessels for containing sterilizing agent for use in sterilizing methods in which instruments to be sterilized are situated in a sterilizing chamber along with a liquid sterilizing agent which evaporates.

Another object of the present invention is to provide an improvement in apparatus for use in the sterilization method disclosed in Finnish Application 874366.

Briefly, in accordance with the present invention, these and other objects are attained by providing a vessel adapted to carry a liquid sterilizing agent wherein the vessel comprises at least two parts, namely, a central, shallow first vessel part defining a central sterilizing agent-containing space, and an outer second vessel part surrounding the central vessel part defining a supplemental space into which the liquid sterilizing agent will flow if it overflows over the short brim wall of the central vessel part while the vessel is being moved. At the same time that the peracetic acid is evaporating, water is also evaporated.

The supplemental liquid sterilizing agent space is preferably about 5 to 20 times are large as the central space for the sterilization agent. In one preferred embodiment, the volume of the supplemental liquid space is about 200 ml, while the volume of the central sterilizing agent space is about 5 to 10 ml. Thus, if there is overflow, the concentrated acid is diluted to the strength of table vinegar.

According to another aspect of the invention, it has been found that the vessel when containing liquid sterilizing agent can be carried in the most stable fashion when the handle is made relatively wide and flat.

DESCRIPTION OF THE DRAWINGS

A more complete appreciation of the present invention and many of the attendant advantages thereof will be readily understood by reference to the following detailed description when considered in connection with the accompanying drawings in which.

DESCRIPTION OF THE PREFERRED EMBODIMENTS

Figure 1:
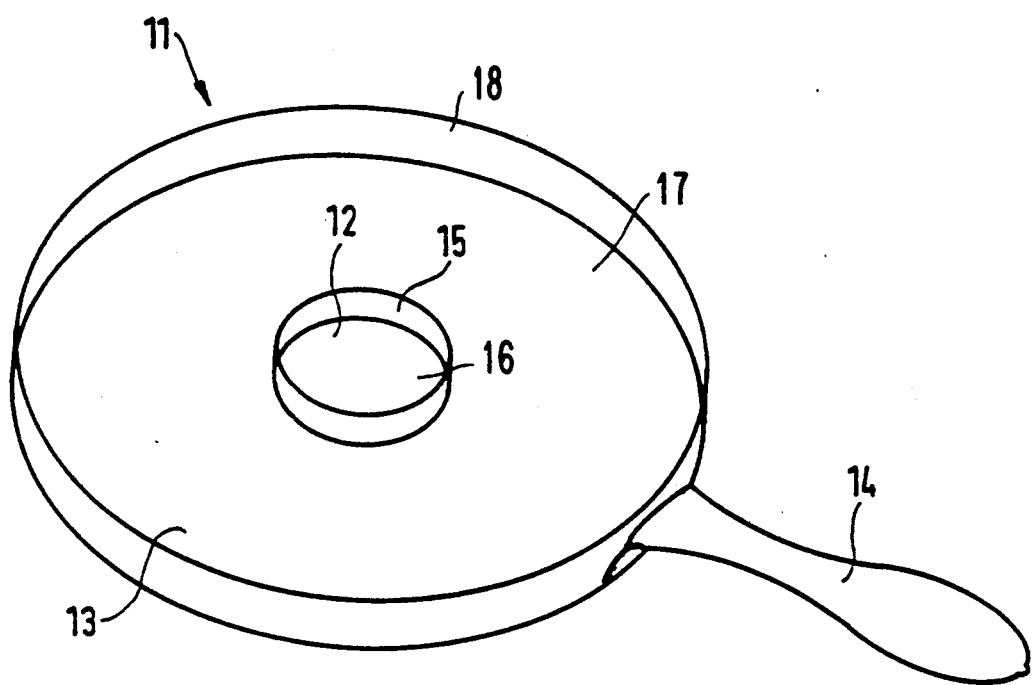
FIG. 1 is a perspective view of a vessel for containing sterilizing agent in accordance with the invention for use in a sterilization method.

Referring now to the figures where like reference characters designate identical or corresponding parts throughout the several views, a vessel in accordance with the invention, generally designated 11, comprises a central, shallow first vessel part 12 including a bottom 16 and a short inner upstanding brim wall 15. The central or first vessel part 12 is designed as a vessel for the sterilizing agent itself and has a sufficient volume to contain the necessary amount of sterilizing agent for a particular sterilization procedure. For example, the volume of the central vessel part 12 is preferably in the range of between about 5 to 10 ml. Since the central sterilization agent-containing space 12 must be shallow to maximize evaporation, the brim 15 must be low. Therefore, when the vessel 11 is moved, the sterilizing agent may overflow or splash over the brim 15.

In order to overcome this problem, the vessel 11 is equipped with an outer vessel part surrounding the central vessel part. The outer vessel part 13 surrounds the central vessel part 12 and includes an annular bottom wall 17 and an outer upstanding brim wall 18. The annular bottom wall 17 and inner and outer brim walls 15, 18 define a supplemental space into which the sterilizing agent will flow if the agent overflows or splashes over the short inner brim wall 15.

The supplemental space defined by the outer vessel part 13 is advantageously dimensioned to accommodate about 200 ml, or a liquid volume that is about 10 to 20 times greater than the amount of peracetic acid thereby assuring that the acid cannot overflow from the supplemental space.

The vessel 11 includes a handle 14 that is connected to the outer brim wall 18. By forming the handle 14 with a wide and flat shape, the vessel 11 can be moved more easily and with greater stability.

Figure 2:
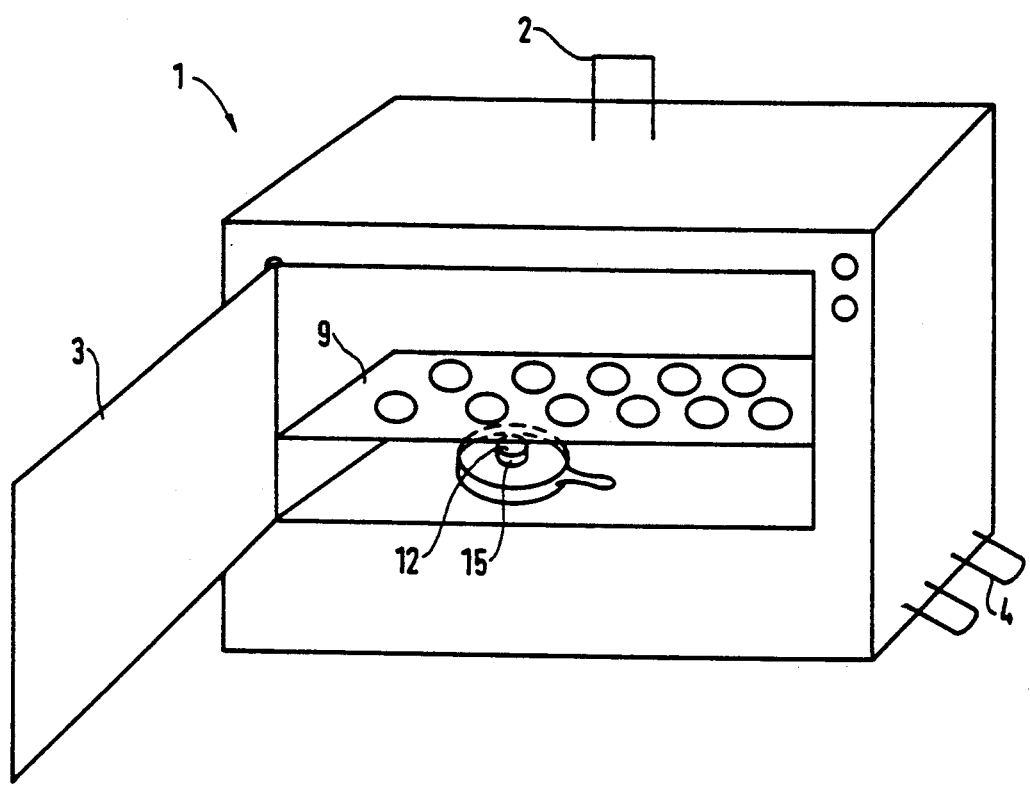
FIG. 2 is a schematic view of apparatus for sterilizing instruments including a vessel for containing sterilizing agent in accordance with the invention.

Referring to FIG. 2, sterilization apparatus, generally designated 1, comprises a cabinet defining a sterilization chamber into which instruments to be sterilized are placed through an openable door 3. The instruments are preferably placed on a grid-like shelf 9. A safety valve 2 is provided at the top of the cabinet. The cabinet 1 is heated to a temperature of about 40° C. by means of a heater 4 which comprises, for example, a glow lamp, a hot-water coil, or a small thermal resistor. The vessel 11 containing peracetic acid in the central shallow space 12 is placed within the chamber of the cabinet 1 below the shelf 9. The sterilizing agent is evaporated by heat conducted through the bottom of the cabinet chamber. Upon completion of the sterilization, the cabinet is emptied such, for example, as by means of a water aspirator or through a hose connected to the ventilation valve, and the vessel 11 containing water is emptied into a wash basin.

Obviously, numerous modifications or variations of the present invention are possible in the light of the above teachings. It is therefore to be understood that within the scope of the claims appended, hereto, the invention may be practiced otherwise than as specifically disclosed herein.

What is claimed is:

1. In an open sterilization vessel for containing liquid sterilizing agent for use in a sterilizing method, said open sterilization vessel being structured to be placed in a closable sterilizing apparatus containing instruments to be sterilized, whereupon the closable chamber is closed and heated to evaporate the liquid sterilizing agent and sterilize the instruments under optimum conditions, the improvement comprising:

said vessel including a central vessel part comprising a bottom and an inner upstanding brim wall defining a central space containing a sterilizing agent, and an outer vessel part surrounding said central vessel part comprising an annular bottom wall and an outer upstanding brim wall, said annular bottom wall and inner and outer brim walls defining a supplemental space containing water into which sterilizing agent will flow if it overflows or splashes over said inner brim wall when the vessel is moved;

said supplemental space having a volume greater than the volume of said central space, and said supplemental space and said central space structured and arranged such that any overflowing sterilizing agent is diluted once it is contained by said supplemental space.

2. The vessel of claim 1 wherein said supplemental space is in the range of between about 5 to 10 times greater than the size of said central space.

3. The vessel of claim 1 wherein said supplemental space has a volume of about 200 ml and said central space for containing sterilizing agent has a volume in the range of between about 5 to 10 ml.

4. The vessel of claim 1 wherein said vessel includes a handle.

5. The vessel of claim 4 wherein said handle is connected to said outer brim wall and has a substantially flat shape.

6. The vessel of claim 4 wherein said handle is connected to said outer brim wall.

7. An arrangement for sterilizing instruments using a liquid sterilizing agent, comprising:

a closable sterilization chamber containing instruments to be sterilized, said chamber including a shelf for holding said instruments, an open sterilization vessel for containing liquid sterilizing agent for sterilizing said instruments, said vessel being structured to be placed in said chamber under said shelf, said vessel having a central vessel part comprising a bottom and an inner upstanding brim wall defining a central space containing a sterilizing agent, and an outer vessel part surrounding said central vessel part comprising an annular bottom wall and an outer upstanding brim wall, said annular bottom wall and inner and outer brim walls defining a supplemental space containing water, said supplemental space having a volume greater than the volume of said central space and being structured and arranged such that said sterilizing agent flows therein if it overflows or splashes over said inner brim wall when said vessel is moved, said closable chamber adapted to be closed and heated to evaporate said liquid sterilizing agent and thereby sterilize said instruments.

* * * * *